(12) United States Patent
Kuo

(10) Patent No.: US 6,360,117 B1
(45) Date of Patent: Mar. 19, 2002

(54) ELECTROCARDIOGRAM SIGNAL COLLECTING APPARATUS

(76) Inventor: Terry B. J. Kuo, 6th Fl., No. 56, Sec. 2, Yung-An N. Rd., Luchou City, Taipei Hsien (TW)

( * ) Notice: Subject to any disclaimer, the term of this patent is extended or adjusted under 35 U.S.C. 154(b) by 0 days.

(21) Appl. No.: 09/317,517

(22) Filed: May 24, 1999

(51) Int. Cl.[7] ................................................ A61B 5/04
(52) U.S. Cl. ...................................................... 600/509
(58) Field of Search ............................... 600/508–527; 607/9, 25

(56) References Cited

U.S. PATENT DOCUMENTS 4,245,650 A * 1/1981 Welker et al.
5,226,431 A * 7/1993 Bible et al.
5,687,734 A * 11/1997 Dempsey et al.
5,876,351 A * 3/1999 Rohde
6,117,076 A * 9/2000 Cassidy

* cited by examiner

Primary Examiner—Mark Bockelman
(74) Attorney, Agent, or Firm—Thorp Reed & Armstrong, LLP

(57) ABSTRACT

An electrocardiogram signal collecting apparatus includes an electrode, a first stage filtering and amplifying section, a second stage filtering and amplifying section, a comparison circuit, a first reference voltage generator, a battery, a battery voltage monitor, a voltage-current converter, a photo-isolator, a current-voltage converter, an analog to digital converter, and a second reference voltage generator. The electrocardiogram signal collection apparatus in accordance with the present invention can be connected to a personal computer or a notebook computer to perform analysis. The electrocardiogram signal collecting apparatus has a simple structure, and occupies a small space. In addition, the electrocardiogram signal collection apparatus is low-cost and easily operated.

9 Claims, 14 Drawing Sheets

ELECTROCARDIOGRAM SIGNAL
COLLECTING
APPARATUS

PC OR NOTEBOOK
COMPUTER

AUTOMATIC REAL-TIME
ANALYSIS
SOFTWARE

ELECTROCARDIOGRAM SIGNAL COLLECTING APPARATUS

BACKGROUND OF THE INVENTION

1. Field of the Invention

The present invention relates to a heart rate variability analyzing system, more particularly, to an electrocardiogram signal collecting apparatus for collecting electrocardiogram signals to be used in heart rate variability analysis. The electrocardiogram signal collecting apparatus in accordance with the present invention is of simple structure and low cost, and can be connected to a personal computer (PC) or a notebook computer.

2. Description of Related Art

The autonomic nervous system closely relates to human health. For example, autonomic ataxia may induce acute or chromic diseases such as cardiac disease, hypertension or even sudden death.

Heart rate variability analysis, which is a non-invasive examination method, has been recognized as a diagnostic indication of the autonomic nervous system. It is found that heart rate variability can be an indicator of the survival rate of a patient suffering severe disease. When a patient's brain pressure increases, his/her heart rate variability will decrease. A brain-dead person's heart rate variability disappears. According to the investigation of Framingham, if an old person's heart rate variability decreases by one standard deviation, then the probability of death for this old person is 1.7 times of the probability for a normal person.

Heart rate variability includes a high-frequency (HF) component and a low-frequency (LF) component. The HF component is synchronous to the breath. The LF component is presumed to be relative to blood vessel movement or pressoreceptor reflex. The low-frequency component can be further divided into a very-low-frequency (VLF) component and LF component.

FIG. 1 is a schematic diagram showing a conventional heart rate variability analyzing system. With reference to FIG. 1, the conventional heart rate variability analyzing system comprises an electrocardiograph, a signal recorder, an analog to digital (A/D) converter and an appropriate analysis computer. In such a system, the measured heart rate needs to be manually corrected. In addition, spectrum analysis software is used in the appropriate analysis computer. The cost of the entire system is very high. Such a system has to be operated by a professional examiner. The operation of such a system comprises two steps: (1) on-line electrocardiogram (ECG) signal recording and (2) off-line analysis. The first step includes collecting ECG signals from a patient with an electrocardiograph and recording the signals on the signal recorder. The first step usually takes about 5 minutes to 24 hours. The second step includes converting the analog signals recorded in the signal recorder into digital signals by the analog to digital converter, transmitting the digital signals to the appropriate analysis computer to perform analysis by using the spectrum analysis software, and correcting the resultant heart rate through manual operation. The second step usually takes about 5 minutes to 2 hours. In practice, there is usually an interval of about 1 minute between these two steps. It is apparent that the conventional heart rate variability analyzing system has some disadvantages. Such a system is very expensive. The operation of the system takes a long period of time. This system occupies a large space. In addition, the system is so complicated that is necessary to be operated by a professional operator. Therefore, such a system is not possible to be used as a personal or home system.

SUMMARY OF THE INVENTION

One object of the present invention is to provide an electrocardiogram signal collecting apparatus, of which the structure is simple and cost is low.

Another object of the present invention is to provide an electrocardiogram signal collecting apparatus, which can be connected to a personal computer (PC) or a notebook computer to perform analysis.

A further object of the present invention is to provide an electrocardiogram signal collecting apparatus, which occupies a small space.

A further object of the present invention is to provide an electrocardiogram signal collecting apparatus, of which the operation takes a short period of time.

A further object of the present invention is to provide an electrocardiogram signal collecting apparatus, which can be operated easily.

In accordance with one aspect of the present invention, the electrocardiogram signal collecting apparatus comprises an electrode to sense heart constriction signals from the patient; a first stage filtering and amplifying section for receiving the signal from the electrode to filter out the DC component and the high frequency component and to amplify the remaining signal; a second stage filtering and amplifying section to further filter and amplify the signal from the first stage filtering and amplifying section; a photo-isolator having an input connected to the signal from the second stage filtering and amplifying section and an output, said output being electrically isolated from said input; an analog to digital converter receiving the photo-isolator output signal to convert said signal into a digital signal; and a printer input/output port connected between said analog to digital converter and a personal computer or notebook computer I/O port for receiving said digital signal from the analog to digital converter and transmitting the output signal to the personal computer or notebook computer.

In accordance with the present invention, the electrocardiogram signal collecting apparatus further comprises a battery to supply power to the first and second stage filtering and amplifying sections.

In accordance with a further aspect of the present invention, the electrocardiogram signal collection apparatus further comprises a battery monitor connected to the battery to monitor the battery power level and provide an alarm to the user when the battery power is low.

Other objects, advantages and novel features of the invention will become more apparent from the following detailed description when taken in conjunction with the accompanying drawings.

DETAILED DESCRIPTION OF PREFERRED EMBODIMENT

Figure 1:
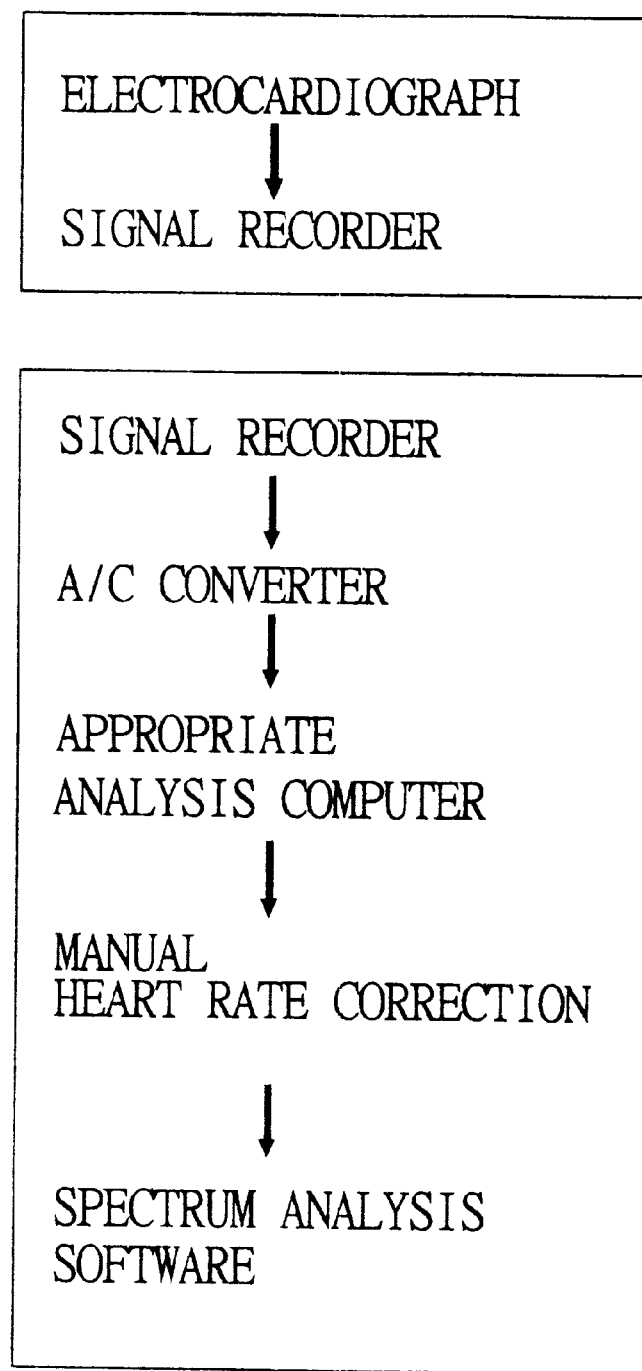
FIG. 1 is a schematic diagram of a conventional heart rate variability analyzing system.
Figure 2:
FIG. 2 is a schematic diagram of a heart rate variability analyzing system using an electrocardiogram signal collecting apparatus in accordance with the present invention.
Figure 2:
Figure 3:
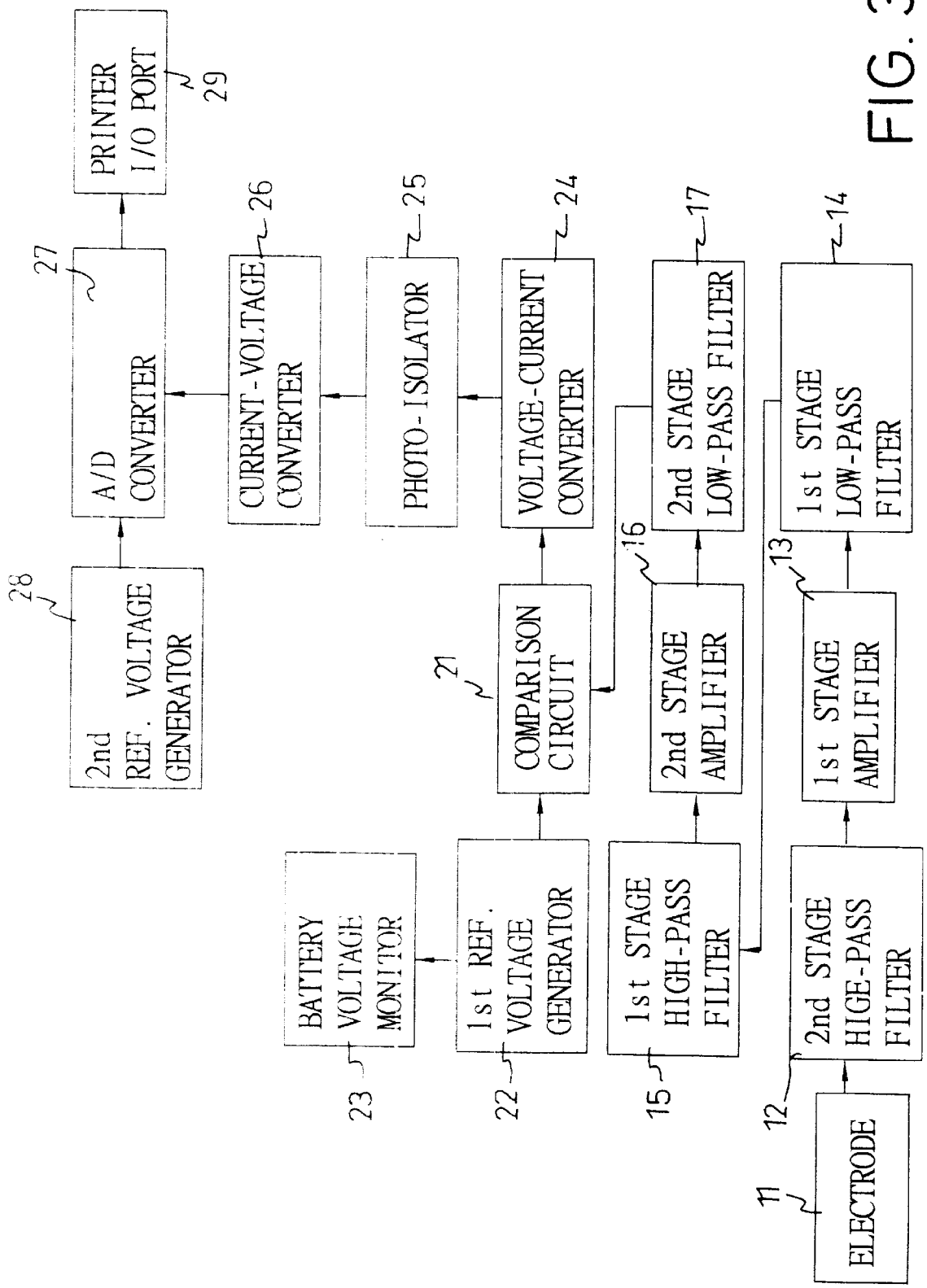
FIG. 3 is a block diagram showing the electrocardiogram signal in accordance with the present invention.
Figure 4A:
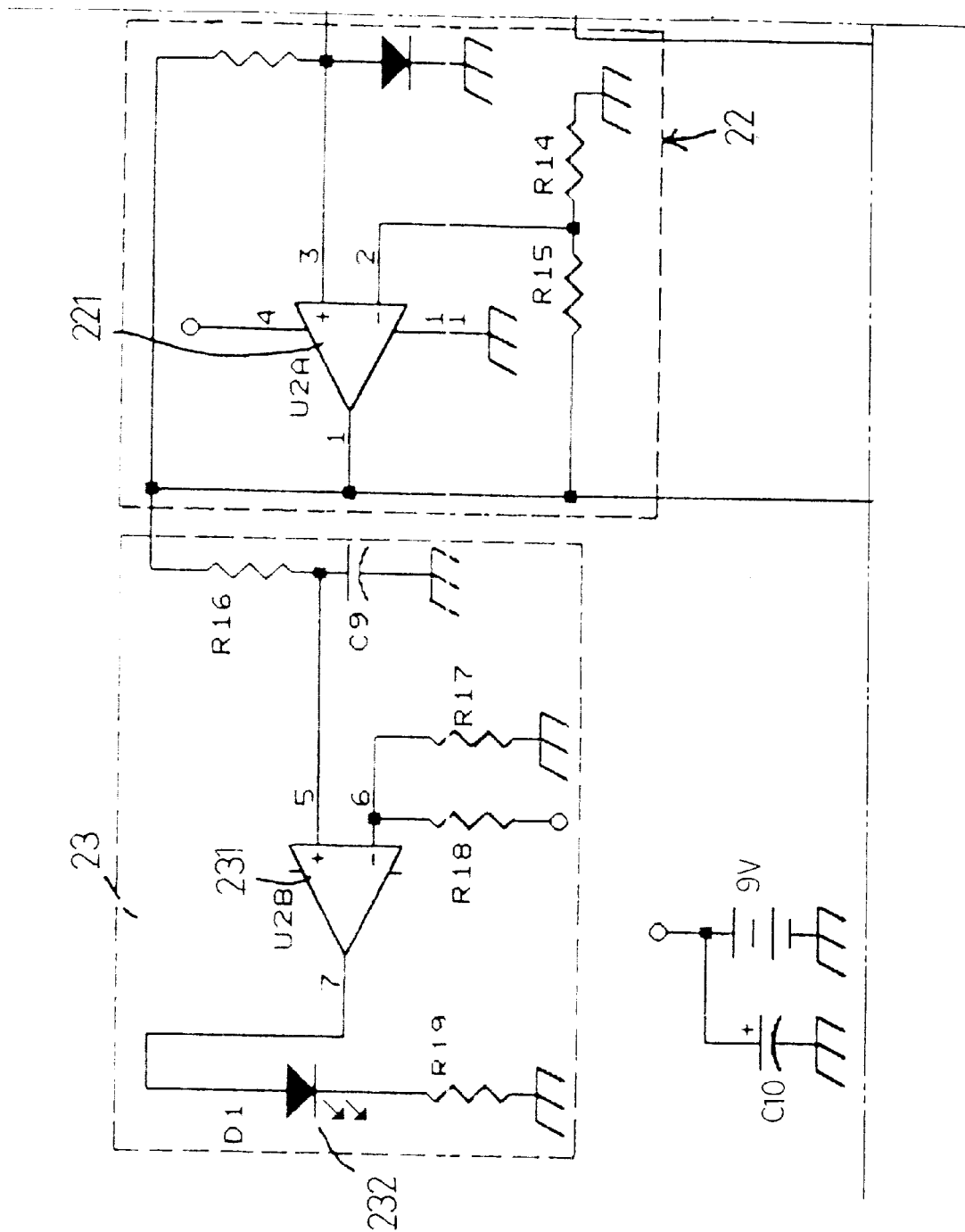
FIGS. 4 and 5 are circuit diagrams of electrocardiogram signal collecting apparatus in accordance with the present invention.
Figure 4B:
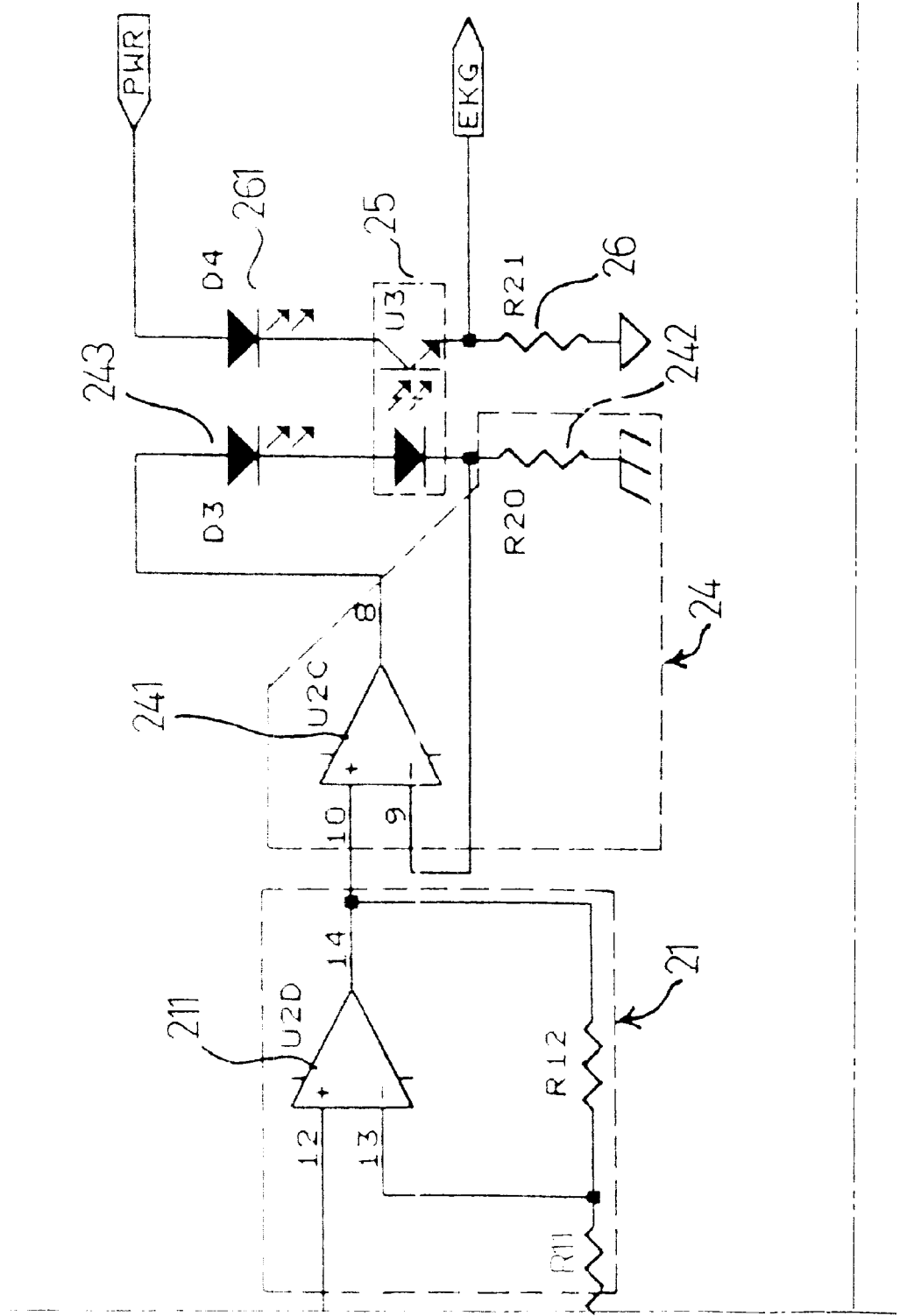
Figure 4C:
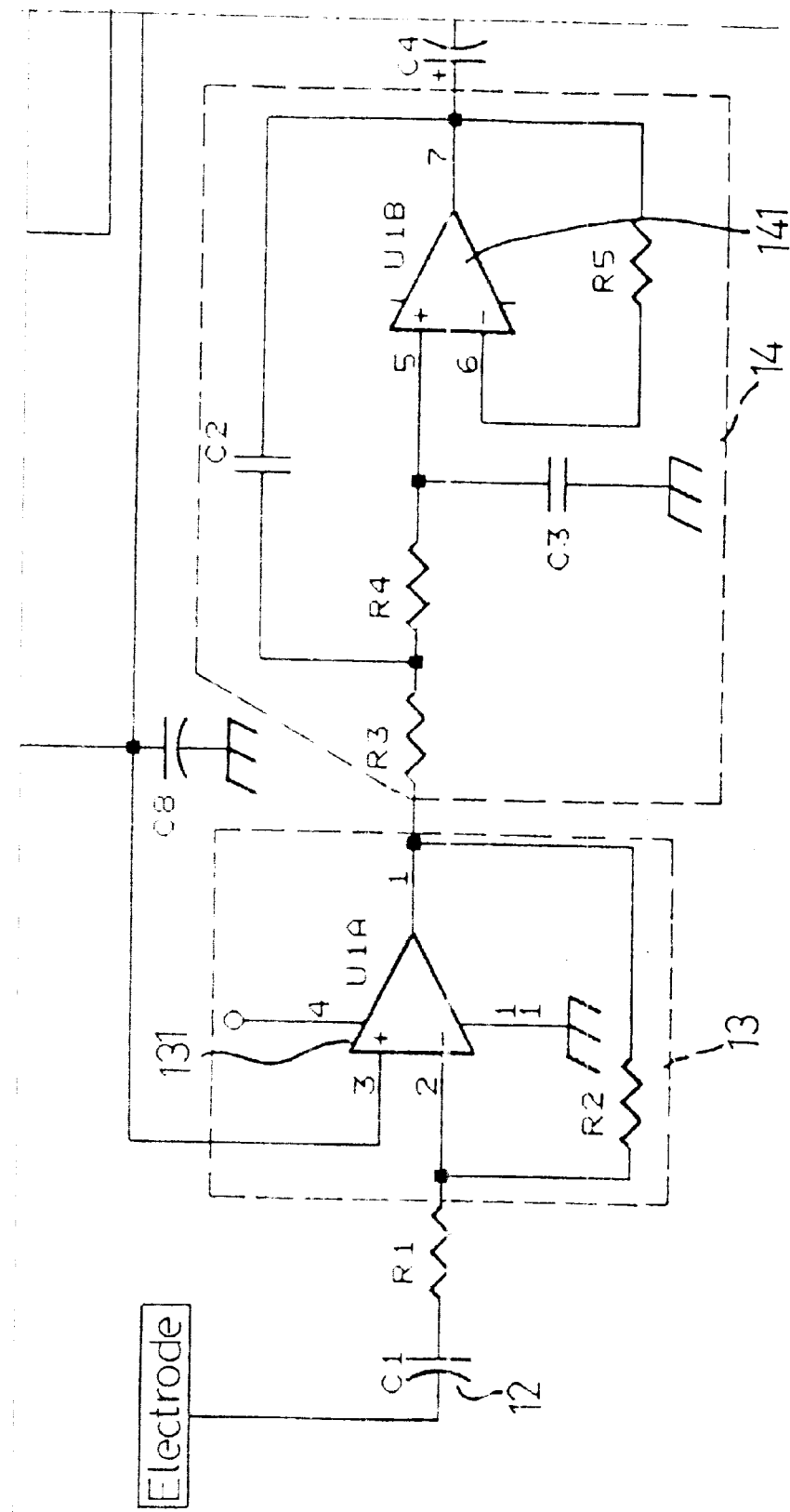
Figure 4D:
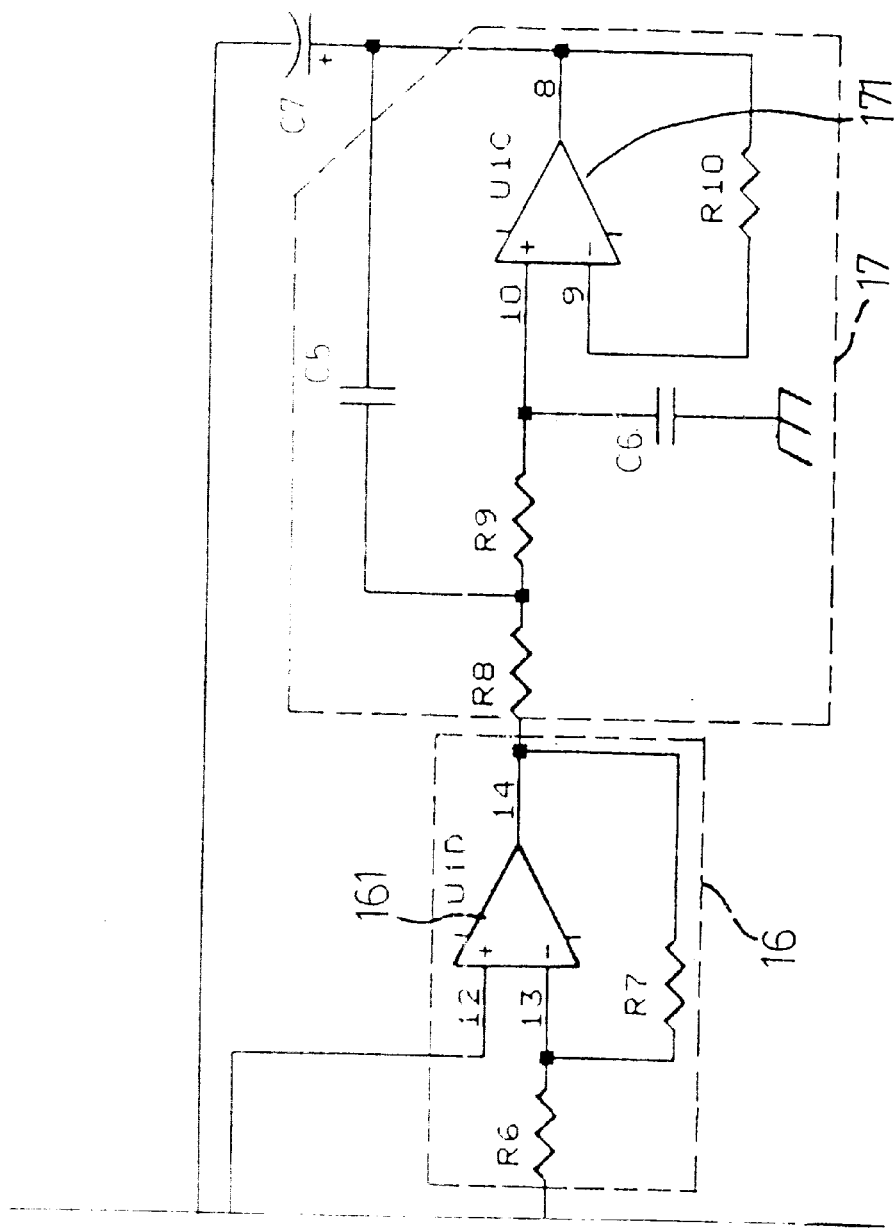

With reference to FIG. 3, an electrocardiogram signal collecting apparatus in accordance with the present invention comprises an electrode (11), a first stage high-pass filter (12), a first stage amplifier (13), a first stage low-pass filter (14), a second stage high-pass filter (15), a second stage amplifier (16), a second stage low-pass filter (7), a comparison circuit (21), a first reference voltage generator (22), a battery voltage monitor (23), a voltage-current converter (24), a photo-isolator (25), a current-voltage converter (26), an analog to digital (A/D) converter (27), and a second reference voltage generator (28).

The first stage high-pass filter (12), the first stage amplifier (13), and the first stage low-pass filter (14) compose a first stage filtering and amplifying section for filtering out the DC component and some high frequency component of the signal and amplifying the level thereof. Similarly, the second stage high-pass filter (15), the second stage amplifier (16), the second stage low-pass filter (17) compose a second filtering and amplifying section.

The electrode (11) is used as an end point to contact the body of a person for detecting a weak voltage signal of heart constriction from the person. The detected signal is transmitted to the first stage high-pass filter (12), the first stage amplifier (13), and a first stage low-pass filter (14) to be filtered and amplified. Then the signal is transmitted to the second stage high-pass filter (15), the second stage amplifier (16), and the second stage low-pass filter (17) to be filtered and amplified again. The resultant signal is transmitted to the comparison circuit (21) to be compared with a reference voltage from the first reference voltage generator (22), so as to eliminate noise and adjust a reference point of the wave of the signal. The signal is then transmitted to the voltage-current converter (24) to be converted into a current signal, so as to drive the photo-isolator (25). Then the current signal is transmitted to the current-voltage converter (26) to be recovered to a voltage signal. The voltage signal is then transmitted to the analog to digital converter (27), which uses a reference voltage from the second reference voltage (28), to be converted to a digital signal. Finally, the digital signal is transmitted to a printer input/output (I/O) port (29), which is compatible with a PC or a notebook computer. The computer then analyzes the signal by utilizing automatic real-time analysis software. The entire operation takes about 5 minutes.

Figure 5:
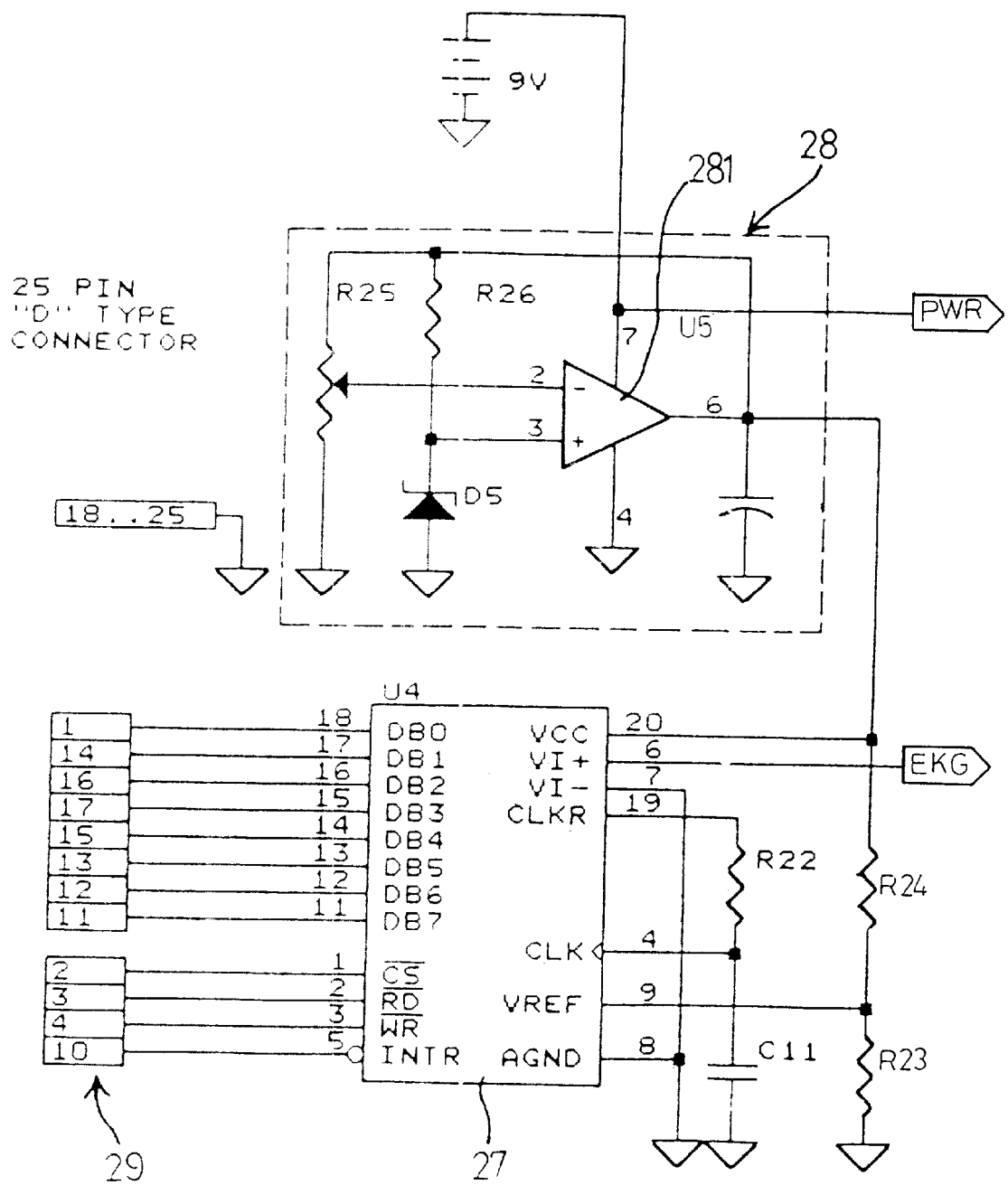

In this embodiment, the respective portions of the electrocardiogram signal collecting apparatus are powered by a 9 volt battery (see FIGS. 4 and 5). The photo-isolator (25) (photo-coupler) isolates the electrocardiogram signal collecting apparatus from the power of the computer. Accordingly, it can prevent the patient from being hurt by the power of the computer. The photo-isolator (25) also isolates the electrocardiogram signal apparatus from interference of noise from the computer. The battery voltage monitor (23) is used to monitor the battery power, and notifying the user when the power of battery is low.

The detail circuitry of the electrocardiogram signal collecting apparatus in accordance with the present invention is shown in FIGS. 4 and 5. As can been seen, each of the first and second stage high-pass filters (12, 15) is implemented with a capacitor to eliminate the DC and VLF (very low frequency) components of the signal. The first stage amplifier (13) comprises an operational amplifier (131) and a negative feedback resistor (R2). The second stage amplifier (16) comprises an operational amplifier (161) and a negative feedback resistor (R7). The first stage low-pass filter (14) comprises an operational amplifier (141), resistors and capacitors. The second stage low-pass filter (17) comprises an operational amplifier (171), resistors and capacitors. The comparison circuit (21), first reference voltage generator (22), battery voltage monitor (23), and voltage-current converter (24) also essentially comprise operational amplifiers (211, 221, 231, 241).

The battery voltage monitor (23) has an indicator (232), which can be an LED. The indicator (231) is turned on when the battery power is low.

The current-voltage converter (24) drives the photo-isolator (25) by an LED (243). The outputs of the photo-isolator (25) are connected to an LED (261) and the current-voltage converter (26), which is a resistor (R21) in this embodiment. The LED (261) is powered by another battery (not shown), which is separate from the battery supplying power to the respective elements of the electrocardiogram signal collecting apparatus. The output voltage signal (EKG) from the current-voltage converter (26) is transmitted into the analog to digital converter (27), which is implemented by a commercially available integrated circuit in this embodiment. The second reference voltage generator (28) also comprises an operational amplifier (281). The reference voltage generated by the second reference voltage generator (28) is sent to the VREF terminal of the analog to digital converter (27).

Figure 6A:
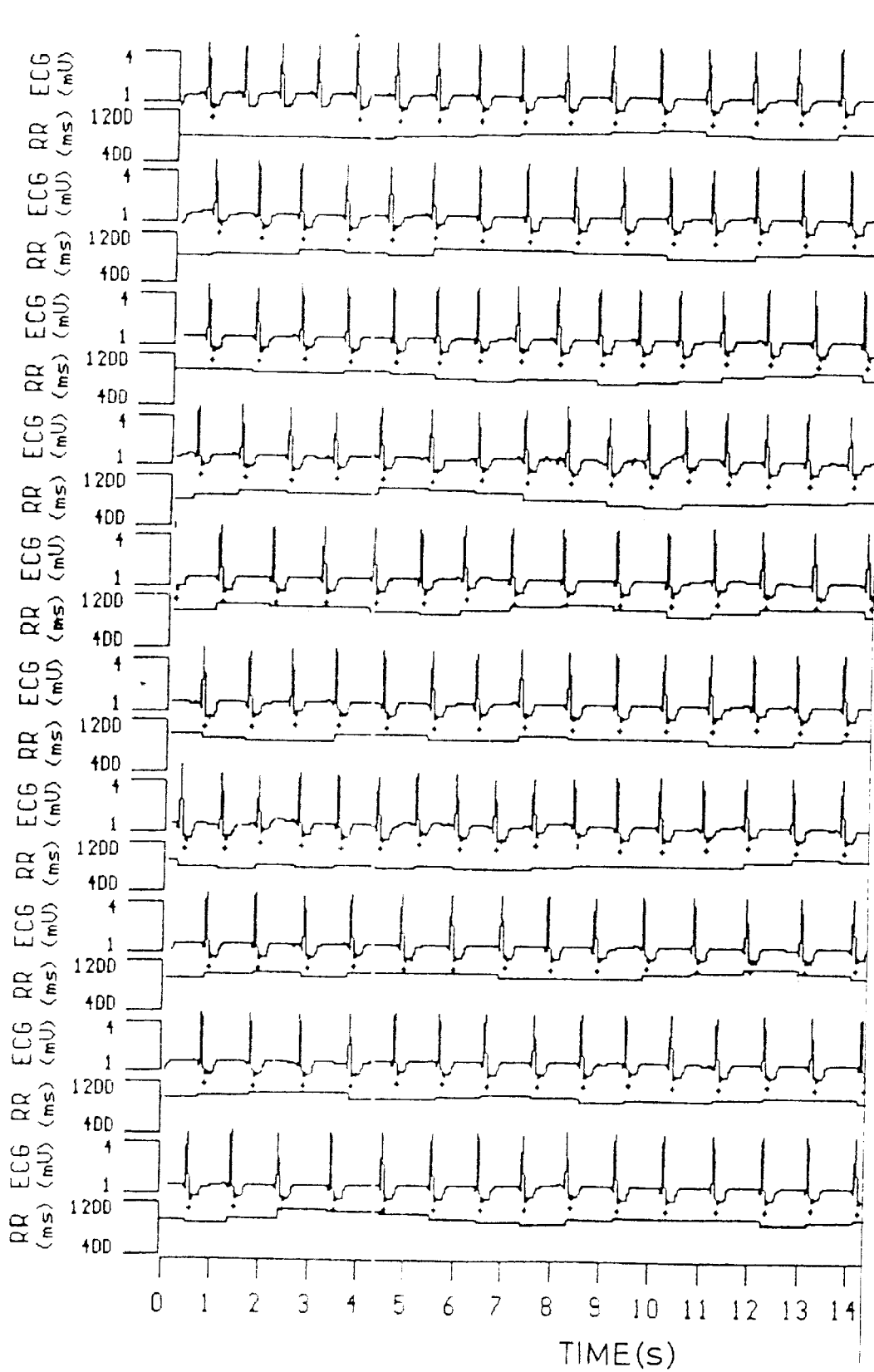
FIG. 6 is electrocardiogram and heart rate cycle data obtained by using the electrocardiogram signal collecting apparatus in accordance with the present invention.
Figure 6B:
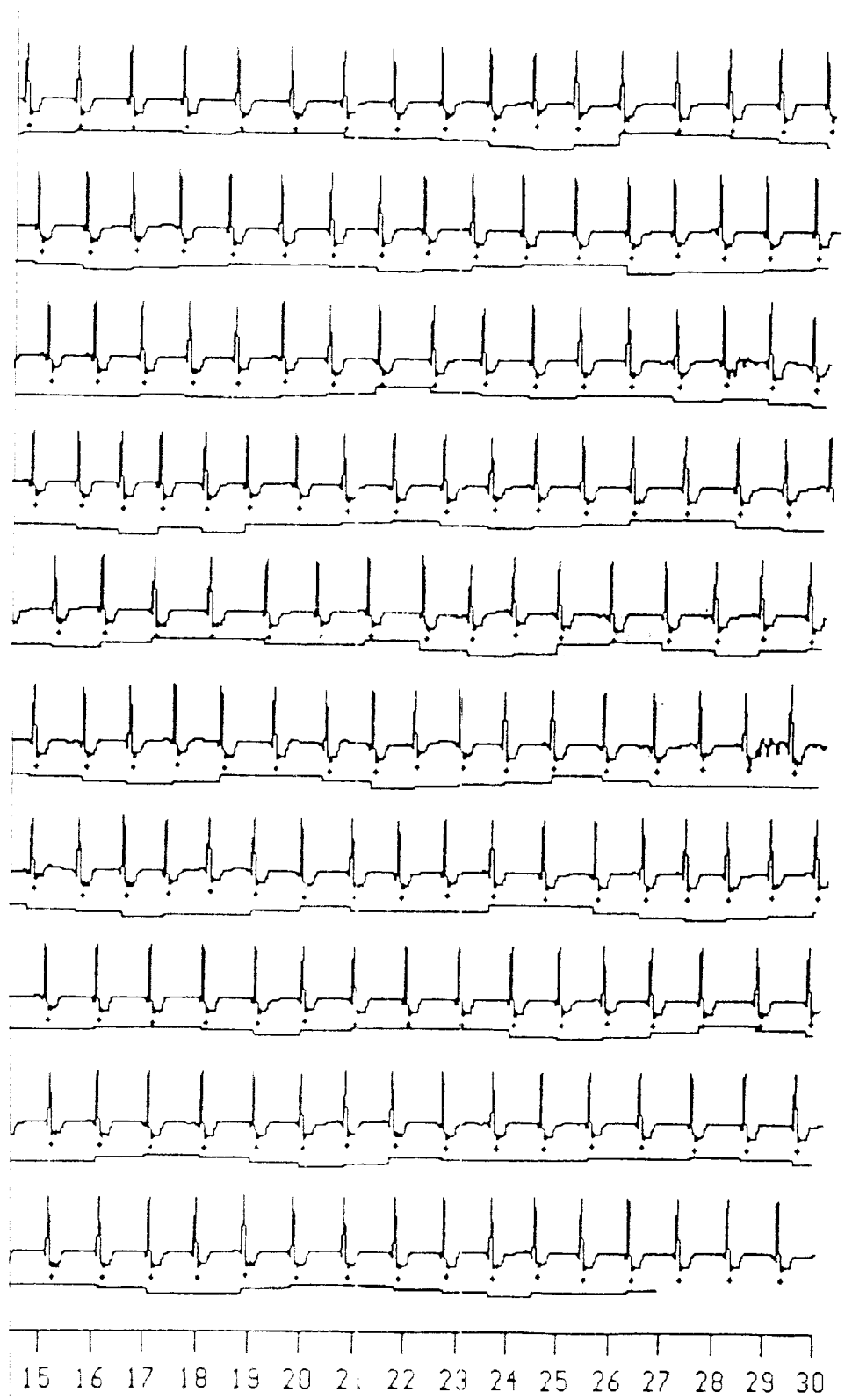

FIG. 6 is electrocardiogram and heart rate cycle data obtained by using the electrocardiogram signal collecting apparatus in accordance with the present invention. In this example, the measurement is performed for 5 minutes with a sample rate of 256 samples per second. A total of 768,000 samples are taken in 5 minutes. In FIG. 6, "ECG" indicates the electrocardiogram, and "RR" indicates the heart rate cycle (beat-to-beat interval).

Figure 7A:
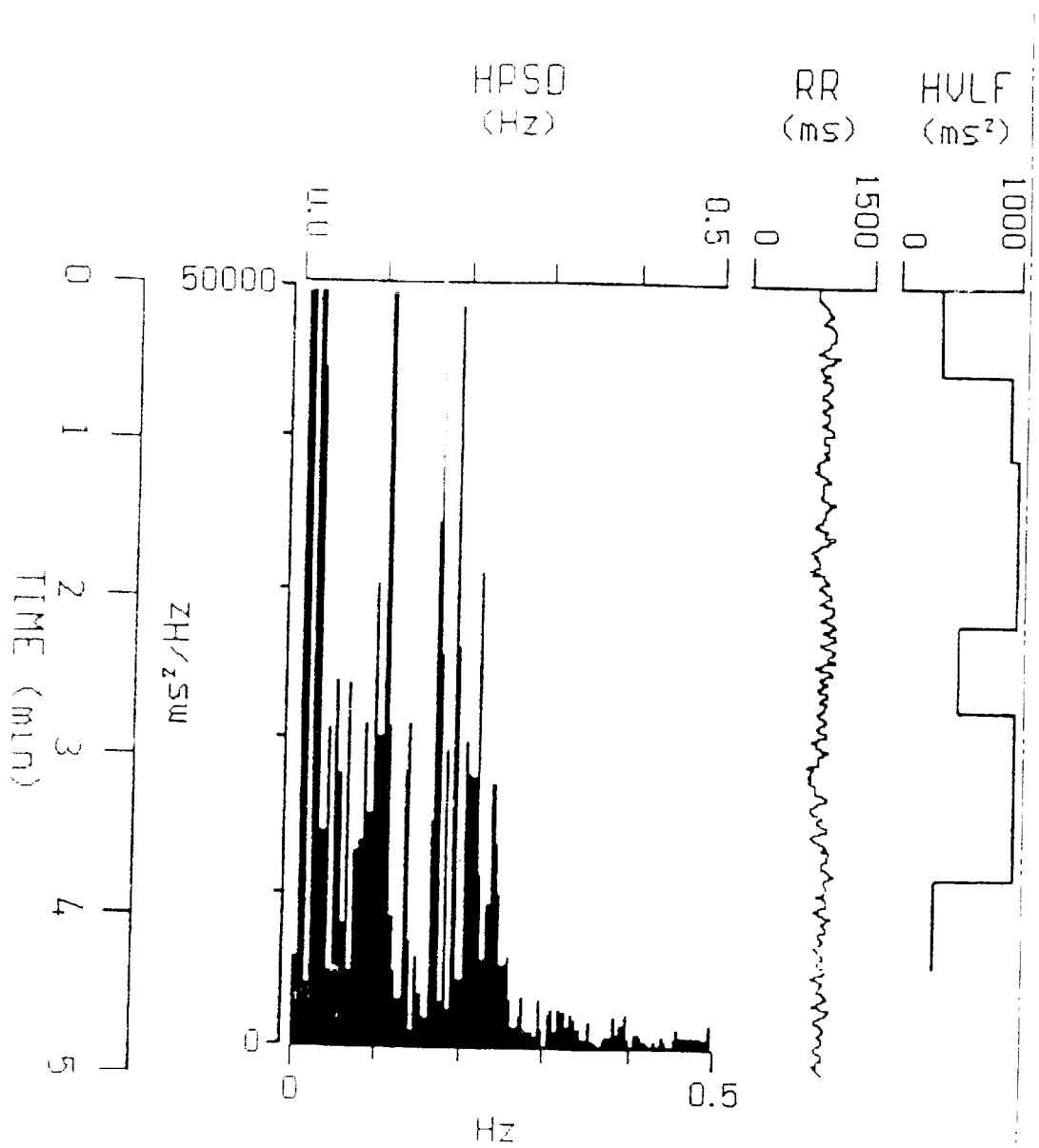
FIG. 7 is the parametric information obtained by analyzing the data of FIG. 6.
Figure 7B:
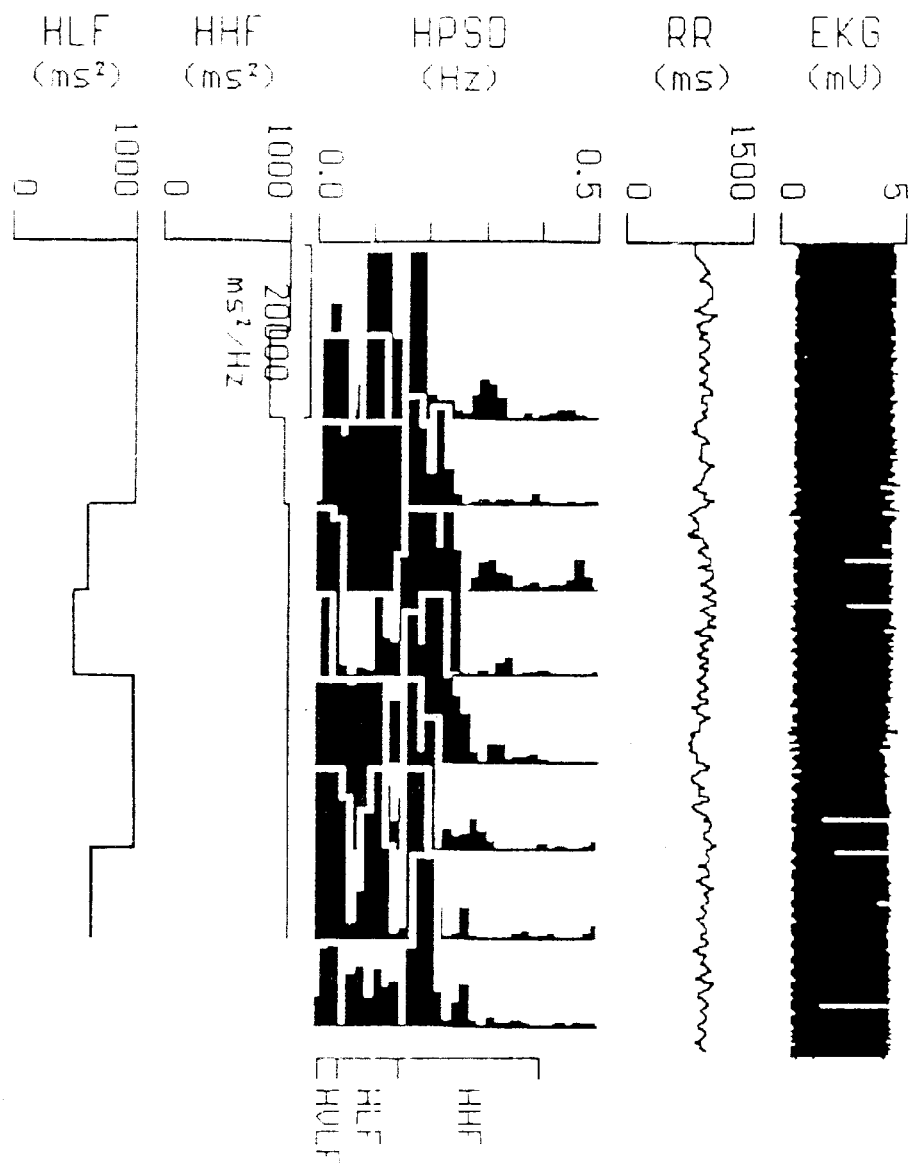
Figure 8A:
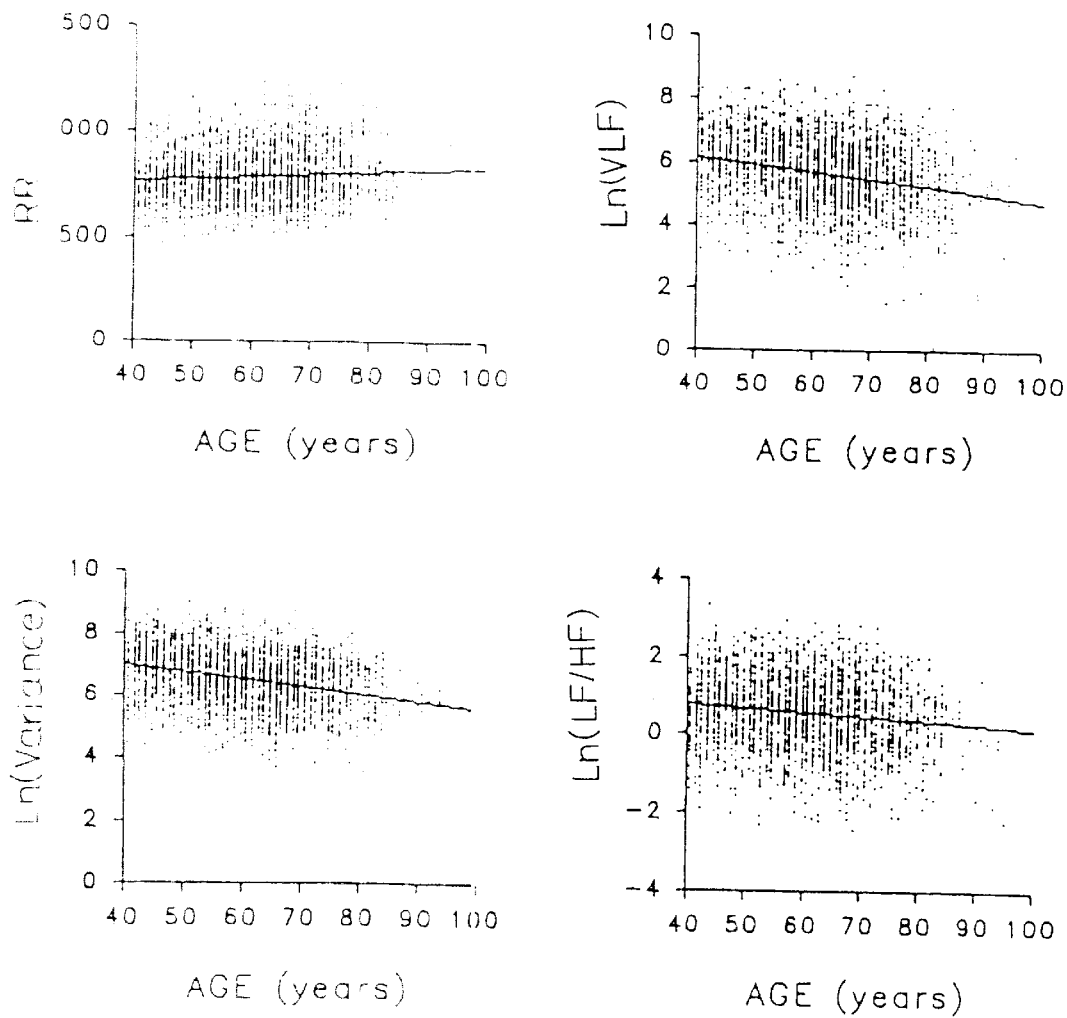
FIG. 8 is a set of graphs to show the relationship between age and the various data obtained by using the electrocardiogram signal collecting apparatus in accordance with the present invention.
Figure 8B:
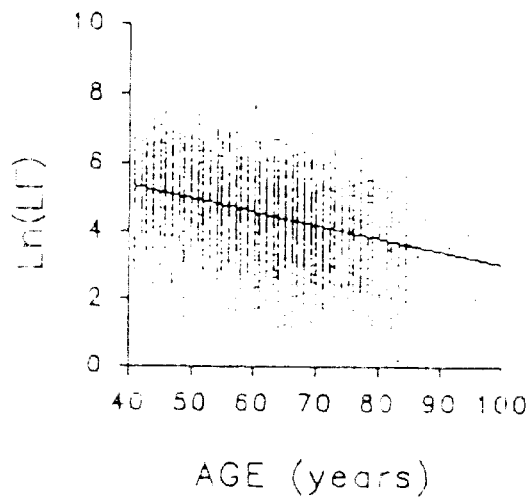
Figure 8B:
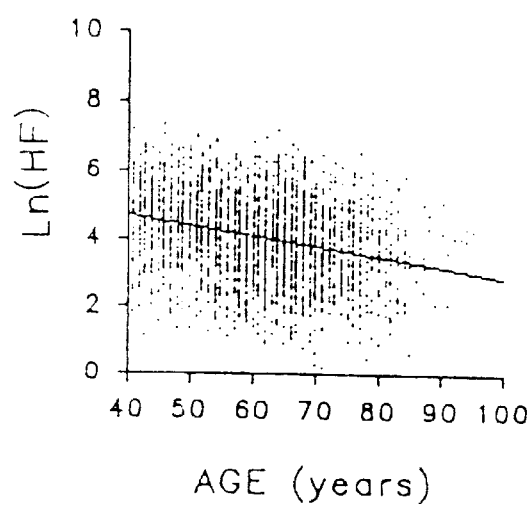
Figure 8B:
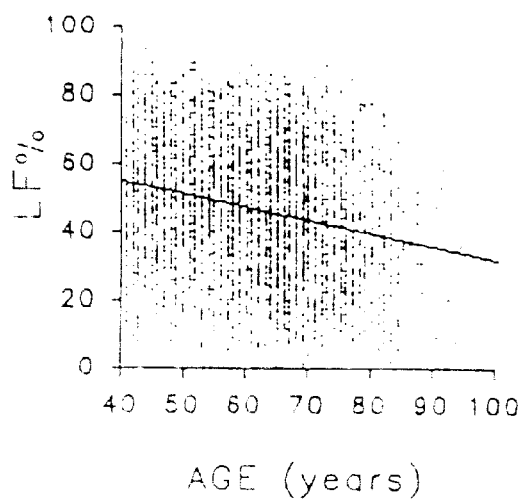
Figure 8B:
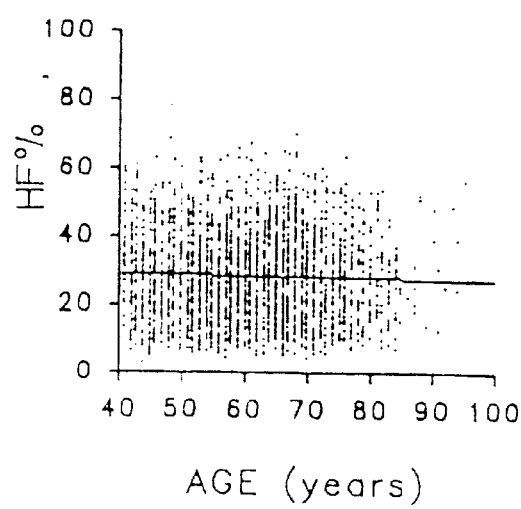

FIG. 7 is parametric information obtained by analyzing the data of FIG. 6. In FIG. 7, "mean" indicates mean heart rate cycle, "VLF" indicates the heart rate variability in the very low frequency range, "LF" indicates the heart rate variability in the low frequency range, "HF" indicates the heart rate variability in the high frequency range, "Var" indicates the total heart rate variability, "LF/HF" indicated the LF to HF ratio, "LF %" indicates standardized LF, "HF %" indicates standardized HF, and "PSD" indicates power density spectrum. FIG. 8 is a set of graphs showing the relationship between age and various data obtained by means of the electrocardiogram signal collecting apparatus in accordance with the present invention. The graphs in FIG. 8 depict the examination data of 2450 persons obtained by the electrocardiogram signal collection apparatus in accordance with the present invention.

What is claimed is:

1. An electrocardiogram signal collecting apparatus comprising:
    an electrode to sense the constriction a person's heart;
    a first stage filtering and amplifying section to filter out the DC component and high frequency component and amplify the signal from the electrode;
    a second stage filtering and amplifying section to further filter and amplify the signal from the first stage filtering and amplifying section;

a photo-isolator to electrically isolate the signal from the second stage filtering and amplifying section and the output;

an analog to digital converter to convert the output of the photo-isolator into a digital signal; and a printer input/output port to serve as an interface between said analog to digital converter and a personal computer or notebook computer printer port.

2. The apparatus as claimed in claim 1, further comprising a battery for supplying power to the first and second stage filtering and amplifying sections.

3. The apparatus as claimed in claim 2, wherein said analog to digital converter is powered by said battery.

4. The apparatus as claimed in claim 2, further comprising a battery monitor connected to said battery for monitoring the battery power and providing an alarm when the battery power is low.

5. The apparatus as claimed in claim 4, wherein said battery monitor comprises an indicator to be turned on when the battery power is low.

6. The apparatus as claimed in claim 1, further comprising a voltage-current converter connected between the second stage filtering and amplifying section and the photo-isolator to convert the signal from the second stage filtering and amplifying section into a current signal to drive the photo-isolator.

7. The apparatus as claimed in claim 6, wherein said voltage-current converter comprises an operational amplifier.

8. The apparatus as claimed in claim 1, wherein said first stage filtering and amplifying section comprises a first stage high-pass filter, a first stage amplifier and a first stage low-pass filter, while the second stage filtering and amplifying section comprises a second stage high-pass filter, a second stage amplifier and a second stage low-pass filter.

9. The apparatus as claimed in claim 8, wherein each of the first stage high-pass filter, first stage amplifier, first stage low-pass filter, second stage high-pass filter, second stage amplifier and second stage low-pass filter comprises an operational amplifier.

\* \* \* \* \*